United States Patent [19]

Dupont et al.

[11] Patent Number: 5,319,128

[45] Date of Patent: * Jun. 7, 1994

[54] PRODUCTION OF TEREPHTHALATE ESTERS BY DEGRADATIVE TRANSESTERIFICATION OF SCRAP OR VIRGIN TEREPHTHALATE POLYESTERS

[75] Inventors: Louis Dupont, Brossard; Ved P. Gupta, Lasalle, both of Canada

[73] Assignee: Synergistics Industries, Ltd., Canada

[ * ] Notice: The portion of the term of this patent subsequent to May 29, 2007 has been disclaimed.

[21] Appl. No.: 860,188

[22] Filed: Mar. 30, 1992

Related U.S. Application Data

[63] Continuation of Ser. No. 494,092, Mar. 15, 1990, Pat. No. 5,101,064.

[51] Int. Cl.$^5$ .................... C07C 67/60; C07C 67/03
[52] U.S. Cl. ........................ 560/78; 560/79; 560/96; 568/868
[58] Field of Search .............. 560/78, 79, 96; 568/868

[56] References Cited

U.S. PATENT DOCUMENTS

| | | | |
|---|---|---|---|
| 3,037,048 | 5/1962 | Lotz | 560/78 |
| 4,578,502 | 3/1986 | Cudmore | 560/79 |
| 4,929,749 | 5/1990 | Gupta et al. | 560/79 |
| 5,101,064 | 3/1992 | Dupont et al. | 560/78 |

FOREIGN PATENT DOCUMENTS

| | | |
|---|---|---|
| 1081681 | 12/1954 | France . |
| 48-097831A | 12/1973 | Japan . |

*Primary Examiner*—Jose' G. Dees
*Assistant Examiner*—Vera C. Clarke
*Attorney, Agent, or Firm*—Larson and Taylor

[57] ABSTRACT

A process for the production of terephthalate diesters having the following formula (I).

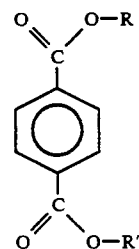

Substituents R and R' are the same or different and represent a straight chain, branched or cyclic aliphatic group, an aromatic group, an alkaryl group or an aralkyl group, each group having from 6 to 20 carbon atoms. The process involves reacting a terephthalate polyester with a high molecular weight alcohol or a mixture of high molecular weight alcohols each having from 6 to 20 carbon atoms, in the presence of a catalyst and recovering the desired compound according to formula (I). This process is particularly useful for recycling scrap terephthalate polyester products such as those produced from polyethylene terephthalate (PET), crystallized polyethylene terephthalate (CPET), glycol-modified polyethylene terephthalate copolyester (PETG), polybutylene terephthalate (PBT), polycyclohexanedimethylene terephthalate (PCT), as well as the acid- and glycol-modified copolyesters of PCT, respectively PCTA and PCTG.

20 Claims, No Drawings

PRODUCTION OF TEREPHTHALATE ESTERS BY DEGRADATIVE TRANSESTERIFICATION OF SCRAP OR VIRGIN TEREPHTHALATE POLYESTERS

This is a continuation of application Ser. No. 07/494,092 filed Mar. 15, 1990, now U.S. Pat. No. 5,101,064.

FIELD OF THE INVENTION

The present invention relates to a process for producing terephthalate diesters through degradative transesterification of terephthalate polyester products. The reactants used for this process are primarily terephthalate polyester products, preferably scrap terephthalate polyester products, thereby providing efficient means for recycling materials such as polyethylene terephthalate (PET), crystallized polyethylene terephthalate (CPET), glycol-modified polyethylene terephthalate copolyester (PETG), polybutylene terephthalate (PBT), polycyclohexanedimethylene terephthalate (PCT), and the acid- and glycol-modified copolyesters of PCT, respectively PCTA and PCTG. This process yields terephthalate diesters which are low to moderate viscosity oils or waxes, which may be useful as plasticizers and presumably as processing aids and/or general purpose lubricants. The plasticizers can be readily used in the preparation of products useful to the plastics industry.

BACKGROUND OF THE INVENTION

Terephthalate polyester resins like PET, CPET, PETG, PBT and PCT are thermoplastic polymers which are widely used in the plastics industry. PET and PETG are used in the manufacturing of film, bottles and plastic containers of all kinds. Virgin PET and PETG resins are approved for food packaging. PET is widely used in the manufacturing of bottles, for both carbonated soft-drink and alcoholic beverages. It is also used in the manufacturing of fabrics and textile materials. CPET and PCTA are used in the manufacturing of dual-ovenable food trays. Filled PET and PBT resins are used in the manufacturing of auto body panels, fenders, bumpers and grilles; relays, iron handles, lawn mower housings and the like.

A major problem with reprocessing terephthalate polyesters is that when heated in the presence of moisture, polyesters may partially hydrolyze to form some free glycol and terephthalic acid in the polymer melt. Polyesters must thus be very dry during processing, typically containing less than 50 ppm moisture, in order to prevent any hydrolysis. Inadvertently, these materials usually do partially hydrolyze during each processing cycle, hence limiting PET's use in the food packaging area to strictly virgin material alone.

With the growing use of terephthalate polyester products, major waste disposal problems and expenses have been encountered by both the manufacturers and the consumers. PET and CPET are currently the most widely used of all the terephthalate polyesters. These compounds are being used to produce consumer products such as bottles for carbonated soft-drink and alcoholic beverages, and dual-ovenable food trays. Typical scrap polyester products are shown in Table I.

TABLE I

| POLYESTER | Typical Scrap Polyester Products PRODUCT |
|---|---|
| PET | * Carbonated Soft-Drink bottle<br>* Beer, Wine or Liquor bottle<br>* Bottles for food products e.g. Mustard<br>* Packaginq film (MYLAR ™)<br>* Photographic/X-Ray film<br>* Fabric/Fibers (DACRON ™, TERYLENE ™)<br>* Auto Fenders (BEXLOY ™) |
| CPET | * Dual ovenable food trays<br>Bottles for |
| PETG | * Personal hygiene products e.g. Shampoo<br>* or Mouthwash<br>* Detergent<br>* Food products |
| PBT | * Auto Bumpers<br>* Auto Grilles<br>* Auto Trim<br>* Distributor Caps |
| PCTA | * Packaging film<br>* Dual ovenable food trays |
| PCT | * High Temperature Engineered parts |
| PCTG | * Sheet/Film for packaging |

There are at present a number of avenues available to recycle or to degrade/depolymerize terephthalate polyesters, PET soft-drink bottles are currently being recycled, but with existing prior art processes, this material must be very clean, free of any contaminants such as bottle cap, paper or plastic labels, glue and high density polyethylene (HDPE) impact-resistant basecups, in order to provide a pure raw material which may be used for products such as carpet backing, pot scourers, fiberfill and the like. The cleaning/segregation process is expensive and adds significant cost to scrap PET. If it is not cleaned, the contaminated PET may sometimes be only used in a low-value non-critical application. On the other hand, the clean PET may possibly be recycled several times. However, during each recycling/processing step, the polyester is further hydrolysed to the point where after several recycling "cycles" the polyester has degraded and shows a significant loss of mechanical properties, at which point it becomes an undesirable product.

When food is cooked in CPET dual-ovenable trays, the polymer is subjected to relatively long periods of moderate heat in the presence of substantial amounts of moisture released from the food. This thermal history as well as the hydrolysis caused by the moisture present during cooking may cause the CPET to degrade to the point where it shows significant loss of mechanical properties. Also, cooking food in the CPET may result in the staining and/or discoloration of the polymer. Hence the degradation and discoloration of CPET make it an undesirable material for recycling and there is at present no recycling effort being made for CPET.

These undesirable materials could either be used in a low-value non-critical application, such as fiber-fill in pillows and sleeping bags, or they could also be recycled by partially depolymerizing the high molecular weight polymer in the presence of a monomer to produce a low molecular weight polymer. These types of processes are disclosed in U.S. Pat. No. 3,037,048.

In U.S. Pat. No. 3,037,048, Lotz discloses a process through which scrap PET products such as filaments, films, fabrics and others are recycled to regenerate the compound dimethyl terephthalate (DMT). This process involves the depolymerization of PET and transesterification in the presence of methanol to yield DMT.

Furthermore, U.S. Pat. No. 4,578,502 issued to Cudmore discloses the use of PET scrap for recovering ethylene glycol and either terephthalic acid or dimethyl terephthalate. The process includes depolymerization of a slurry of scrap PET by hydrolysis or methanolysis, and subsequently crystallization of the desired product. The disclosure of U.S. Pat. No. 4,578,502 is limited to the production of dimethyl terephthalate. In fact, at column 3, lines 22-28 of this document, it is stated that it is preferable not to use alcohols of a higher molecular weight than methanol.

It should be noted that in order to obtain a value-added product from scrap terephthalate polyester using the processes referred to in U.S. Pat. No. 3,037,048 (col. 2, line 64) and U.S. Pat. No. 4,578,502 (col. 3, lines 58-59), the use of extreme high-pressure reactors is required, hence involving a major capital investment for the set-up.

Hence, most of the PET/polyester recycling processes using transesterification presently known in the art are mainly aimed at producing starting materials that could be used for the synthesis of new terephthalate products. Therefore, it would be interesting to provide a one step process for the recycling of terephthalate polyesters that would yield products that could be readily used either in the plastics industry or otherwise. Plasticizers, lubricants, waxes and the like are good examples of these useful products of which plasticizers are readily usable products for the plastics industry.

Plasticizers are crucial constituents in the preparation of some plastic products. For example, dioctyl terephthalate (DOTP) is particularly useful to the PVC industry. Esters of this type can be synthesized mainly by reacting terephthalic acid with a suitable alcohol. Unfortunately in this case, the esterification reaction is very slow, thereby making the process economically undesirable. Alternatively, the transesterification of dimethyl terephthalate to DOTP through its reaction with 2-ethyl hexanol is an interesting reaction that yields DOTP rather quickly.

Therefore, suitable recycling alternatives that would yield a product of good commercial value would be highly desirable.

SUMMARY OF THE INVENTION

In accordance with the present invention, there is provided a process for producing a compound having the following formula (I):

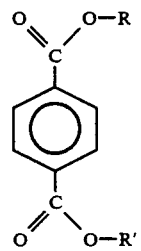

In formula (I), substituents R and R' are the same or different and represent a straight chain, branched or cyclic aliphatic group, an aromatic group, an alkaryl group or an aralkyl group, each group having from 6 to 20 carbon atoms. Preferably, R and R' are the same or different and represent a straight chain or branched alkyl group having from 6 to 20 carbon atoms. The process involves reacting a terephthalate polyester product with a high molecular weight alcohol or a mixture of high molecular weight alcohols each having from 6 to 20 carbon atoms, in the presence of a catalyst and recovering the compound according to formula (I).

Also within the scope of the present invention is a process for recycling filled or unfilled scrap terephthalate polyesters into terephthalate diesters. The process comprises reacting filled or unfilled scrap terephthalate polyesters with a high molecular weight alcohol having from 6 to 20 carbon atoms or a mixture of high molecular weight alcohols each having from 6 to 20 carbon atoms in the presence of a catalyst at a temperature ranging from 160° to 260° C. and recovering the desired terephthalate diester.

Preferably, the terephthalate ester source will come from scrap terephthalate polyester products although it is to be understood that any suitable terephthalate polyester source (virgin, scrap or off-spec material) could be used in the context of the present invention. The carbon atom content of the alcohol to be used in the process of the present invention will correspond to the desired carbon atom content of substituents R and R'.

Hence, it has been discovered that scrap terephthalate polyester products can be successfully recycled through transesterification with higher alcohols to yield valuable compounds. Preferably, terephthalate polyesters such as scrap PET, PETG, CPET or PBT can be recycled to desirable products useful to the industry. It is to be noted, that in the context of the present invention, the term "recycle" when used herein is intended to define a process through which scrap material such as PET, PETG, CPET, PBT or PCT and its copolyesters PCTA and PCTG, is used as a starting material for producing terephthalate esters such as plasticizers.

The process of the present invention constitutes a clearly unexpected advance in terephthalate polyester products recycling for example, considering the fact that the teachings of pertinent literature on PET recycling such as U.S. Pat. No. 4,578,502 clearly leads away from the use of higher alcohols in reactions involving PET scrap.

Furthermore, the process of this invention can be carried out in standard esterification reactors which operate either at atmospheric pressure, under partial vacuum or under slight pressurization, that is a pressure of about 30 psi or less. This constitutes a further improvement over prior art processes which usually require the use of expensive high-pressure reactors. Also, since the products derived from the process of the present invention are liquids, or may be easily liquified by slight heating, and hence easily filtered, the use of contaminated (paper, caps, HDPE) scrap terephthalate polyesters may thus be contemplated. This is because the filtration of a low viscosity liquid is much simpler than that of a highly viscous polymer melt. The potential use of contaminated scrap would greatly reduce the cost of the recycled terephthalate polyester, and hence product derived therefrom.

The advantages of the process of the present invention would be more readily illustrated by referring to the following description.

DETAILED DESCRIPTION OF THE INVENTION

The present invention relates to a process for producing terephthalate diesters. The process is useful for recycling scrap terephthalate polyester products such as PET; used to produce bottles, photographic/X-ray or packaging film and fabric, CPET used to produce dualovenable food trays as well as filled PET and PBT resin that is used to produce auto body panels, fenders, bumpers and the like.

Generally speaking, the process of the present invention involves the transesterification of a terephthalate polyester product at temperature that can vary between 160° and 260° C. preferably between 185° and 240° C., using a straight chain, branched or cyclic aliphatic alcohol or using an aromatic, alkaryl or aralkyl alcohol, the alcohol used having a carbon atom content ranging from 6 to 20 inclusively. The choice of the alcohol is obviously dependent upon the desired final product and although a straight chain or branched alcohol having from 6 to 20 carbon atoms is preferred, it is to be understood that a wide variety of alcohols may be used in the context of the present invention. It is to be mentioned that since transesterification reactions are performed with catalysts, the use of any suitable esterification or transesterification catalyst may be contemplated. Tin based catalysts such as stannous oxalate are preferred in the context of the present invention.

The temperature at which transesterification of most terephthalate polyesters occurs is relatively high. It will usually range between 185° and 240° C. However, a number of suitable alcohols that could be used in the process of the present invention have boiling points that are lower than the desirable transesterification temperature. This minor difficulty may be overcome by slightly pressurizing the reaction vessel or by adding suitable amounts of the final product to the initial reaction mixture in order to raise its overall boiling point. In some instances, however, it may also be necessary to carry out the process under vacuum. Preferably, the reaction may be carried out under partial vacuum of 23"/Hg up to a pressure of 30 psi.

It is to be noted that in certain instances it may be desirable to use a mixture of alcohols for performing the process of the present invention. In the case of an alcohol mixture containing two alcohols, three different compounds would be obtained, one where both substituents R and R' would bear the alkyl/aryl portion of the first alcohol, one where both substituents R and R' would bear the alkyl/aryl portion of the second alcohol and one where substituants R and R' would bear different alkyl/aryl groups. The proportions of the alcohols forming the desired alcohol mixture will vary depending on the targeted composition of the final products.

The transesterification reactors to be used in the context of the present invention to produce the terephthalate esters may be of two types, either i) a pressure reactor design or ii) an esterification reactor operating at atmospheric pressure.

i) Pressure Reactor Design and Operation

This type of reactor is used in instances where the boiling point of the alcohol or mixture of alcohols is lower than the optimum reaction temperature.

The pressure reactor may, for example, consist of a 500 c.c. vessel, capable of being heated to 250° C., fitted to a 400 c.c. Dean & Stark trap or to any apparatus which may be used to perform the same function. The trap may be fitted with a condenser used to help remove the glycol by-product.

Typically 0.25 mole equivalents (approximately 50 grams) of chopped scrap PET along with 1.0 mole equivalents (approximately 130 grams) of alcohol and 0.3 gram of tin catalyst are placed in the 500 c.c. reactor. The Dean & Stark trap is filled with 200 grams of water and 200 grams of alcohol. The assembled pressure reactor is then evacuated to a vacuum level of 28-29 inches of mercury and refilled with inert carbon dioxide gas to a pressure of 5-10 psi. The reactor is heated to a temperature ranging between 185° and 240° C., preferably to between 205°-235° C. for a period ranging from 4 to 12 hours and preferably from 4 to 7 hours, depending on the type of alcohol used. Reaction by-products such as ethylene glycol may distill off during the reaction process.

It is to be noted that the removal of glycol and/or the addition of an excess of alcohol may accelerate the transesterification reaction. Because there is no bubbling of inert gas in this reactor, normally used to drive vapors towards the condenser, an excess of alcohol, preferably a 100 percent excess, may be used to accelerate the reaction.

The removal of ethylene glycol from the (distilling) alcohol/glycol condensate may be achieved by ensuring a suitable amount of water, which may range from 5 to 400 c.c. but which will preferably range from 150 to 250 c.c., is present in the 400 c.c. Dean & Stark trap or in any apparatus which may be used to perform the same function. It is to be mentioned that any substance being a solvent for glycol and in which alcohols having from 6 to 20 carbon atoms are not soluble may be used in the context of the present invention.

At the end of the reaction, glycol which may have distilled off, will be in solution in the water contained in the Dean & Stark trap. Also about 0.25 moles of the desired terephthalate diester corresponding approximately to the number of mole equivalents of PET initially placed in the reactor, some residual glycol along with the original 100 percent excess plus some overflowing alcohol from the Dean & Stark trap are found in the reaction vessel.

ii) Atmospheric Esterification Reactor and Operation

This type of reactor can be used for an alcohol or a mixture of alcohols having a boiling point in the operating range of the reaction. Alternatively, alcohol or a mixture of alcohols having a boiling point inferior to the optimum operating temperature may be used in this equipment if suitable amount of the final product is added to raise its boiling point to within the operating temperature range.

This reactor typically consists of a 5 liter, 5 neck round bottom reaction vessel fitted with a 500 c.c. Dean & Stark trap or any apparatus which may be used to perform a similar function followed by a 400 m.m. double-jacketed condenser. To ensure minimum loss of alcohol and/or glycol, the vapour exiting the top of the condenser is fed through a cold trap chilled by dry-ice, followed by a Friedrich condenser. Any condensate is allowed to drip back into the Dean & Stark trap. This reactor is not pressurized and operates at atmospheric pressure or may be operated under partial vacuum.

Typically 2.5 mole equivalents (approximately 500 grams) of chopped scrap PET along with 6 mole equivalents (approximately 800-1800 grams) of alcohol (a 20 percent excess) and 1.5 grams of tin catalyst are placed in the 5 liter vessel. The 500 c.c. Dean & Stark trap is filled with between 50 and 450 c.c. of water, preferably with between 250 and 350 cc. of water and 200 grams of alcohol. The reactor is heated to between 165° and 260° C., preferably to between 205° and 260° C., under a continuous stream of inert carbon dioxide gas (bubbled in), for a period of time ranging from 3 to 12 hours, preferably from 3 to 6 hours depending on the type of alcohol used. Some of the glycol by-product may be removed to the water layer in the Dean & Stark trap. Partial vacuum may be applied to help the refluxing of the alcohol(s), thus promoting the removal of the glycol.

At the end of the reaction any glycol which may have distilled off will be in solution in the water in the trap. Also about 2.5 moles of the desired terephthalate diester corresponding approximately to the number of mole equivalents of PET initially placed in the reactor, some residual glycol along with the original 20 percent excess alcohol plus some overflowing alcohol from the Dean & Stark trap are found in the reaction vessel.

Typical examples of the products that can be obtained using the process of the present invention include di normal hexyl terephthalate, dioctyl terephthalate, di n-octyl n-decyl terephthalate, diisononyl terephthalate, diisodecyl terephthalate, di n-tridecyl n-pentadecyl terephthalate and diisoeicosyl terephthalate.

The following examples are included in order to further illustrate rather than limit the scope of the present invention.

Examples 1 to 7 illustrate the preparation of terephthalate esters using scrap PET as raw material.

EXAMPLE 1

Preparation of di normal hexyl terephthalate (DNHTP) from scrap PET 100 grams (0.52 mole equivalents) of chopped scrap PET from clear soft-drink bottle, 128 grams (1.25 moles) of normal hexanol and 0.3 gram of stannous oxalate were placed into a 500 c.c. pressure vessel. To the Dean & Stark trap was added 206 grams water and 206 grams n-hexanol. The reactor was pressurized to 8 psi pressure with carbon dioxide gas and then was heated from room temperature to about 207° C. over a period of three hours and maintained at about 207° C. for an additional period of eight hours. Gas chromatography analysis of the final product revealed the presence of DNHTP. The removal of residual n-hexanol and ethylene glycol from the ester was achieved by steam distillation (stripping) of DNHTP under vacuum. The distillation vessel was heated from room temperature to about 150° C. over a period of three hours. The product had an acidity equivalent before washing of 0.95 mg KOH/g product. The ester was washed, dried and filtered after which a total of 107 grams (0.32 mole) of the final product was recovered. This indicates an overall yield of 61 percent. The final product was a wax at room temperature, with a melting point range of 56°–59° C. The glycol by-product recovered had a refractive index of 1.4298 at 23° C.

EXAMPLE 2

Preparation of dioctyl terephthalate (DOTP) from scrap PET

Scrap PET (clear soft-drink bottle) was reacted with 2-ethyl hexanol. Refer to Example 1 for the general outline of the procedure. Refer to Table II for the reaction conditions. Refer to Table III for the diester properties.

EXAMPLE 3

Preparation of diisononyl terephthalate (DINTP) from scrap PET

Scrap PET (green soft-drink bottle) was reacted with isonoyl alcohol. Refer to Example 4 for the general outline of the procedure. Refer to Table II for the reaction conditions.

EXAMPLE 4

Preparation of diisodecyl terephthalate (DIDTP) from scrap PET 430 grams (2.24 mole equivalents) of chopped scrap PET (clear soft-drink bottle), 848 grams (5.36 moles) of isodecanol and 0.98 gram of stannous oxalate were placed into the 5 liter reaction vessel. To the Dean & Stark trap was added 300 grams of water and 188 grams of isodecanol. The reaction mixture was heated, under a continuous stream of inert carbon dioxide gas (bubbled in), from room temperature to about 229° C. over a period of two hours, and was maintained at about 229° C. for an additional period of four hours. Gas chromatography analysis of the final product revealed the presence of DIDTP, 101 grams (1.63 moles) of ethylene glycol distilled off during the transesterification reaction and was present in the water layer in the Dean & Stark trap. The removal of residual isodecanol and ethylene glycol from the ester was achieved by steam distillation (stripping) of DIDTP under vacuum. The distillation vessel was heated from room temperature to 147° C. over a period of six hours, after which 978 grams (2.19 moles) of the desired product was recovered, indicating a 98 percent yield after stripping. The product had an acidity equivalent before washing of 0.22 mg KOH/g product. The ester was washed, dried and then filtered. The final product had an acid number of 0.09 mg KOH/g, a density of 0.971 g/c.c. at 23° C. and a refractive index of 1.4914 at 23° C.

EXAMPLE 5

Preparation of di n-octyl n-decyl terephthalate (DNODTP) from scrap PET

Scrap PET (clear soft-drink bottle) was reacted with a 50/50 blend of n-octanol and n-decanol sold under the trade name Alfol 810. Refer to Example 4 for the general outline of the procedure. Refer to Table II for the reaction conditions. Refer to Table III for the diester properties. The resulting product was a wax at room temperature, with a melting point range of 33°–34° C.

EXAMPLE 6

Preparation of di n-tridecyl n-pentadecyl terephthalate (DNTDPDTP) from scrap PET Scrap PET (clear soft-drink bottle) was reacted with a 70/30 blend of n-tridecanol and n-pentadecanol sold under the trade name of Exxal L1315. Refer to Example 4 for the general outline of the procedure. Refer to Table II for the reaction conditions. Refer to Table III for the diester properties. The resulting product was a wax at room temperature, with a melting point range of 45°–46° C.

EXAMPLE 7

Preparation of diisoeicosyl terephthalate (DIETP) from scrap PET

Scrap PET (clear soft-drink bottle) was reacted with isoeicosyl alcohol sold under the trade name of Exxal 20 (isoarachidyl) alcohol. Refer to Example 4 for the general outline of the procedure. Refer to Table II for the reaction conditions. Refer to Table III for the diester properties.

Examples 8 and 9 illustrate the preparation of terephthalate esters using scrap CPET as raw material.

EXAMPLE 8

Preparation of di normal hexyl terephthalate (DNHTP) from scrap CPET

Scrap CPET (dual-ovenable food tray) was reacted with normal hexanol. Refer to Example 1 for the general outline of the procedure. Refer to Table II for the reaction conditions. Refer to Table III for the diester properties.

EXAMPLE 9

Preparation of diisoeicosyl terephthalate (DIETP) from scrap CPET

Scrap CPET (dual-ovenable food tray) was reacted with isoeicosyl alcohol. Refer to Example 4 for the general outline of the procedure. Refer to Table II for the reaction conditions. Refer to Table III for the diester properties.

Examples 10 and 11 illustrate the preparation of terephthalate esters using PETG as raw material.

EXAMPLE 10

Preparation of di normal hexyl terephthalate (DNHTP) from PETG

PETG resin was reacted with normal hexanol. Refer to Example 1 for the general outline of the procedure. Refer to Table II for the reaction conditions. Refer to Table III for the diester properties.

EXAMPLE 11

Preparation of diisoeicosyl terephthalate (DIETP) from PETG

PETG resin was reacted with isoeicosyl alcohol. Refer to Example 4 for the general outline of the procedure. Refer to Table II for the reaction conditions. Refer to Table III for the diester properties.

Examples 12 and 13 illustrate the preparation of terephthalate esters using PBT as raw material.

EXAMPLE 12

Preparation of di normal hexyl terephthalate (DNHTP) from PBT

PBT resin was reacted with normal hexanol. Refer to Example 1 for the general outline of the procedure. Refer to Table II for the reaction conditions. Refer to Table III for the diester properties.

EXAMPLE 13

Preparation of diisoeicosyl terephthalate (DIETP) from PBT

PBT resin was reacted with isoeicosyl alcohol. Refer to Example 4 for the general outline of the procedure. Refer to Table II for the reaction conditions. Refer to Table III for the diester properties.

TABLE II

| | Reactor Charge and Operation Conditions used in Example 1 to 13 | | | | | |
| --- | --- | --- | --- | --- | --- | --- |
| DIESTER PRODUCT | Ex. No. | POLYESTER WEIGHT g. | ALCOHOL WEIGHT g. | AVERAGE TEMP. °C. | CONDIT. A/P/VAC | DIESTER YIELD % |
| | | PRODUCTS FROM PET | | | | |
| DNHTP | 1 | 100 | 128 | 207 ± 7 | PRESS. | 61.4 |
| DOTP | 2 | 100 | 162 | 225 ± 9 | PRESS. | 62.1 |
| DINTP | 3 | 230 | 462 | 211 ± 4 | ATM. | N/A |
| DIDTP | 4 | 430 | 848 | 229 ± 7 | ATM. | 97.9 |
| DNODTP | 5 | 459 | 827 | 224 ± 11 | ATM. | 97.3 |
| DNTDPDTP | 6 | 344 | 921 | 224 ± 19 | P.VAC. | 95.2 |
| DIETP | 7 | 264 | 985 | 248 ± 13 | P.VAC. | 98.2 |
| | | PRODUCTS FROM CPET | | | | |
| DNHTP | 8 | 48 | 102 | 226 ± 5 | PRESS. | 72.8 |
| DIETP | 9 | 268 | 985 | 245 ± 9 | P.VAC. | 80.9 |
| | | PRODUCTS FROM PETG | | | | |
| DNHTP | 10 | 48 | 102 | 226 ± 1 | PRESS. | 55.2 |
| DIETP | 11 | 264 | 985 | 239 ± 10 | P.VAC. | 70.6 |
| | | PRODUCTS FROM PBT | | | | |
| DNHTP | 12 | 55 | 102 | 212 ± 3 | PRESS. | 69.8 |
| DIETP | 13 | 303 | 987 | 252 ± 6 | P.VAC. | 75.9 |

KEY
N/A Not Available
PRESS. Reactor is pressurized, but no more than 30 psi.
ATM. Reactor operates at atmospheric pressure.
P.VAC. Reactor operates under partial vacuum, up to 23"/Hg.

TABLE III

| | | Diester Properties | | |
| --- | --- | --- | --- | --- |
| DIESTER PRODUCT | Ex. No. | DENSITY q/c.c. | ACID NUMBER mg KOH/g | ESTER CONTENT % |
| | | PRODUCTS FROM PET | | |
| DNHTP | 1 | N/A | N/A | 91.7 |
| DOTP | 2 | .987 | 0.15 | 97.9 |
| DINTP | 3 | N/A | N/A | 94.9 |
| DIDTP | 4 | .971 | 0.09 | 99.6 |
| DNODTP | 5 | N/A | 0.24 | 99.8 |
| DNTDPDTP | 6 | N/A | 0.24 | 97.4 |
| DIETP | 7 | .922 | 0.12 | 99.9 |
| | | PRODUCTS FROM CPET | | |
| DNHTP | 8 | N/A | 0.24 | 97.9 |
| DIETP | 9 | .916 | 0.32 | 97.2 |
| | | PRODUCTS FROM PETG | | |
| DNHTP | 10 | N/A | 0.14 | 93.4 |
| DIETP | 11 | .931 | 0.03 | 94.3 |
| | | PRODUCTS FROM PBT | | |
| DNHTP | 12 | N/A | 0.55 | 94.2 |
| DIETP | 13 | .924 | 0.03 | 86.5 |

KEY
N/A Not Available

We claim:

1. A process for producing a compound having the following formula (I):

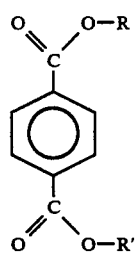

wherein R and R' are the same or different and represent a straight chain, branched or cyclic aliphatic group, an aromatic group, an alkaryl group or an aralkyl group, each group having from 6 to 20 carbon atoms, said process comprising reacting a terephthalate polyester with a high molecular weight alcohol or mixture of high molecular weight alcohols each having from 6 to 20 carbon atoms, in the presence of a catalyst and recovering the compound according to formula (I).

2. A process according to claim 1, wherein R and R' are the same or different and represent a straight chain or branched alkyl group having from 6 to 20 carbon atoms.

3. A process according to claim 1, wherein said terephthalate polyester is reacted with said high molecular weight alcohol or mixture of high molecular weight alcohols under partial vacuum of 23"/Hg up to a pressure of 30 psi.

4. A process according to claim 1, wherein an excess of said high molecular weight alcohol or mixture of high molecular weight alcohols is reacted with said terephthalate polyester.

5. A process according to claim 1, wherein the reaction is carried out at a temperature ranging between 160° and 260° C.

6. A process according to claim 1, wherein said terephthalate polyester is reacted with said high molecular weight alcohol or mixture of high molecular weight alcohols in a reactor comprising a reaction vessel and a Dean & Stark trap or any apparatus performing the same function.

7. A process according to claim 6, wherein a substance being a solvent for glycol and in which alcohols having from 6 to 20 carbon atoms are not soluble is added in said Dean & Stark trap, thereby enhancing removal of reaction by-products.

8. A process according to claim 7, wherein said substance is water.

9. A process according to claim 1, wherein said terephthalate polyester is selected from the group consisting of polyethylene terephthalate, crystallized polyethylene terephthalate, glycol-modified polyethylene terephthalate copolyester, polybutylene terephthalate and polycyclohexanedimethylene terephthalate and acid- and glycol-modified copolyesters thereof.

10. A process according to claim 1, wherein said high molecular weight alcohol is selected from the group consisting of normal hexanol, 2-ethyl hexanol, isononanol, isodecanol, isoeicosanol, normal octanol, normal decanol, normal tridecanol and normal pentadecanol.

11. A process according to claim 1, wherein said mixture of high molecular weight alcohols is selected from the group consisting of a mixture of normal octanol and normal decanol and a mixture of normal tridecanol and normal pentadecanol.

12. A process according to claim 1, wherein the compound recovered according to formula I is selected from the group consisting of di normal hexyl terephthalate, dioctyl terephthalate, diisononyl terephthalate, diisodecyl terephthalate, di-n-octyl n-decyl terephthalate, di-n-tridecyl n-pentadecyl terephthalate and diisoeicosyl terephthalate.

13. A process for recycling filled or unfilled scrap terephthalate polyesters into terephthalate diesters, said process comprising reacting filled or unfilled scrap terephthalate polyesters with a high molecular weight alcohol having from 6 to 20 carbon atoms or a mixture of high molecular weight alcohols each having from 6 to 20 carbon atoms in the presence of a catalyst at a temperature ranging from 160° to 260° C. and recovering the desired terephthalate diester.

14. A process according to claim 13, wherein said terephthalate polyester is selected from the group consisting of polyethylene terephthalate, crystallized polyethylene terephthalate, glycol-modified polyethylene terephthalate copolyester, polybutylene terephthalate and polycyclohexanedimethylene terephthalate and acid- and glycol-modified copolyesters thereof.

15. A process according to claim 13, wherein said terephthalate polyester is reacted with said high molecular weight alcohol or mixture of high molecular weight alcohols under partial vacuum of 23"/Hg up to a pressure of 30 psi.

16. A process according to claim 15, wherein the terephthalate polyester is polyethylene terephthalate.

17. A process according to claim 15, wherein the terephthalate polyester is crystallized polyethylene terephthalate.

18. A process according to claim 15, wherein the terephthalate polyester is glycol-modified polyethylene terephthalate copolyester.

19. A process according to claim 15, wherein the terephthalate polyester is polybutylene terephthalate.

20. A process for producing a compound having the following formula (I):

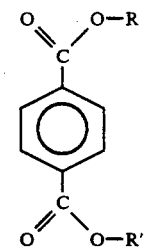

wherein R and R' are the same or different and represent a straight chain, branched or cyclic aliphatic group, an aromatic group, an alkaryl group or an aralkyl group, each group having from 6 to 20 carbon atoms, said process comprising:
 reacting a terephthalate polyester with an alcohol or mixture of alcohols having from 6 to 20 carbon atoms in the presence of a catalyst;
 allowing glycol by-product to be distilled off during the reaction process; said reaction being conducted in a reactor comprising a reaction vessel in a Dean-Stark trap or any apparatus performing the same function, said apparatus having therein a solvent for said glycol by-product in which alcohols having from 6 to 20 carbons are not soluble; and
 recovering the compound according to formula (I).

* * * * *